(12) United States Patent
Wang et al.

(10) Patent No.: US 7,785,320 B2
(45) Date of Patent: *Aug. 31, 2010

(54) METHOD FOR OPERATING A MEDICAL ROBOTIC SYSTEM BY STOPPING MOVEMENT OF A SURGICAL INSTRUMENT ABOUT A PIVOT POINT OR ISSUING A WARNING IF THE PIVOT POINT MOVES BEYOND A THRESHOLD VALUE

(75) Inventors: Yulun Wang, Goleta, CA (US); Darrin R Uecker, Santa Barbara, CA (US); Jeff Wilson, Santa Barbara, CA (US); Keith Philip Laby, Santa Barbara, CA (US); Steve Jordan, Santa Barbara, CA (US); James Wright, Santa Barbara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/051,957

(22) Filed: Mar. 20, 2008

(65) Prior Publication Data

US 2008/0221731 A1 Sep. 11, 2008

Related U.S. Application Data

(63) Continuation of application No. 11/357,383, filed on Feb. 17, 2006, now Pat. No. 7,390,325, which is a continuation of application No. 10/310,405, filed on Dec. 4, 2002, now Pat. No. 7,027,892, which is a continuation of application No. 09/000,934, filed on Dec. 30, 1997, now Pat. No. 6,905,491, which is a continuation of application No. 08/603,543, filed on Feb. 20, 1996, now Pat. No. 5,762,458, and a continuation-in-part of application No. 08/903,914, filed on Jul. 31, 1997, now Pat. No. 5,815,640, which is a continuation of application No. 08/613,866, filed on Mar. 11, 1996, now Pat. No. 5,907,664, which is a continuation of application No. 08/072,982, filed on Jun. 3, 1993, now Pat. No. 5,524,180, which is a continuation-in-part of application No. 08/005,604, filed on Jan. 19, 1993, now abandoned, which is a continuation-in-part of application No. 07/927,801, filed on Aug. 10, 1992, now abandoned.

(51) Int. Cl.
*A61B 17/00* (2006.01)
(52) U.S. Cl. .................................. 606/1; 901/2; 901/9
(58) Field of Classification Search .................. 606/1, 606/10, 11, 13, 41, 43, 106, 107, 130; 600/101–104, 600/106–109, 114; 704/3, 200–210, 231; 700/245–264; 901/2, 6, 8–10, 14–18, 30, 901/36, 46; 414/2, 4–6
See application file for complete search history.

(56) References Cited

U.S. PATENT DOCUMENTS 4,979,949 A 12/1990 Matsen, III et al.

(Continued)

FOREIGN PATENT DOCUMENTS

WO WO-9501757 1/1995

OTHER PUBLICATIONS

Adams, Ludwig et al., Computer-Assisted Surgery, IEEE Computer, May 1990, pp. 43-52, vol. 10—Issue 3, IEEE Computer Society Press.

(Continued)

*Primary Examiner*—Ahmed M Farah

(57) ABSTRACT

A system for performing minimally invasive cardiac procedures. The system includes a pair of surgical instruments that are coupled to a pair of robotic arms. The instruments have end effectors that can be manipulated to hold and suture tissue. The robotic arms are coupled to pair of master handles by a controller. The handles can be moved by the surgeon to produce a corresponding movement of the end effectors. The controller controls and limits movement of robotic arms relative to the patient.

2 Claims, 7 Drawing Sheets

U.S. PATENT DOCUMENTS

| | | | |
|---|---|---|---|
| 5,078,140 | A | 1/1992 | Kwoh |
| 5,086,401 | A | 2/1992 | Glassman et al. |
| 5,184,601 | A | 2/1993 | Putman |
| 5,217,003 | A | 6/1993 | Wilk |
| 5,236,432 | A * | 8/1993 | Matsen et al. .................. 606/88 |
| 5,279,309 | A | 1/1994 | Taylor et al. |
| 5,305,203 | A | 4/1994 | Raab |
| 5,339,799 | A | 8/1994 | Kami et al. |
| 5,402,801 | A | 4/1995 | Taylor |
| 5,417,210 | A | 5/1995 | Funda et al. |
| 5,515,478 | A | 5/1996 | Wang |
| 5,622,170 | A * | 4/1997 | Schulz ....................... 600/424 |
| 5,631,973 | A | 5/1997 | Green |
| 5,697,939 | A | 12/1997 | Kubota et al. |
| 5,762,458 | A | 6/1998 | Wang et al. |
| 5,784,542 | A | 7/1998 | Ohm et al. |
| 5,808,665 | A | 9/1998 | Green |
| 5,855,553 | A | 1/1999 | Tajima et al. |
| 5,876,325 | A | 3/1999 | Mizuno et al. |
| 5,887,121 | A | 3/1999 | Funda et al. |
| 6,102,850 | A | 8/2000 | Wang et al. |
| 6,132,368 | A | 10/2000 | Cooper |
| 6,223,100 | B1 * | 4/2001 | Green ........................ 700/264 |
| 6,468,265 | B1 * | 10/2002 | Evans et al. .................... 606/1 |
| 6,905,491 | B1 | 6/2005 | Wang et al. |
| 7,027,892 | B2 * | 4/2006 | Wang et al. ................. 700/245 |

OTHER PUBLICATIONS

Alexander, Arthur D., A Survey Study of Teleoperators Robotics and Remote Systems Technology, Remotely Manned Systems—Exploration and Operation in Space, California Institute of Technology, 1973.

Alexander, Arthur D. III, Impacts of Telemation on modern society, First CISM-IFToMM Symposium, Sep. 5, 1973, pp. 122-136, vol. 2.

Mair, Gordon M., Industrial Robotics, Prentice Hall, 1988, pp. 41-43,49-50,54,203-209.

Preising, B. et al., A Literature Review: Robots in Medicine, IEEE Engineering in Medicine and Biology, 1991, pp. 13-22, 71, vol. 10—Issue 2, IEEE.

Rasor, Ned S. et al., Endocorporeal Surgery Using Remote Manipulators, Proceedings of the First National Conference held at California Institute of Technology, 1972, pp. 483-492.

Schenker, Paul S. et al., "Development of a Telemanipulator for Dexterity Enhanced Microsurgery", 2ndAnnual International Symposium on Medical Robotics and Computer Assisted Surgery, Nov. 4-7,Baltimore, Maryland, 1995, pp. 81-88.

Schurr, M.O et al., Experimental Telemanipulation in Endoscopic Surgery, Surgical Laparoscopy and Endoscopy, 1996, pp. 167-175, vol. 6—Issue 3.

Sukthankar, Sujat M. et al., Force Feedback Issues in Minimally Invasive Surgery, Interactive Technology and the New Paradigm for Healthcare, 1995, pp. 375-379, vol. 56, IOS Press and Ohmsha.

Taylor, Russell H. et al., A Telerobotic Assistant for Laparoscopic Surgery, IEEE Engineering in Medicine and Biology, May/Jun. 1995, pp. 279-288, vol. 14—Issue 3, IEEE.

Tendick, Frank et al., "Analysis of the Surgeon's Grasp of Telerobotic Surgical manipulation," IEEE Engineering in Medicine & Biology Society 11th Annual International Conference, 1989, 2 Pages.

Vertut, Jean et al., Robot Technology: Teleoperation and Robotics Evolution and Development, 1986, 5 Pages, vol. 3A, Hermes Publishing.

* cited by examiner

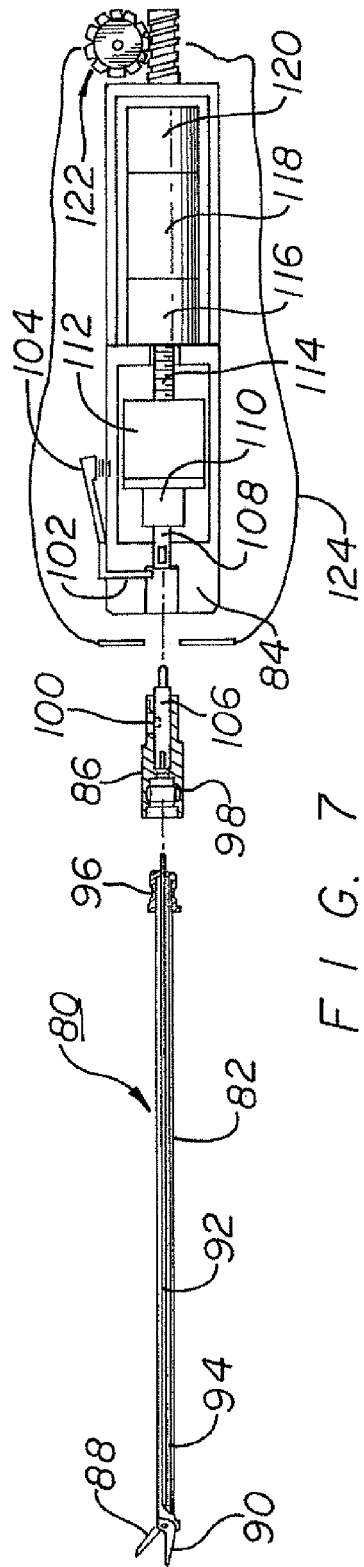
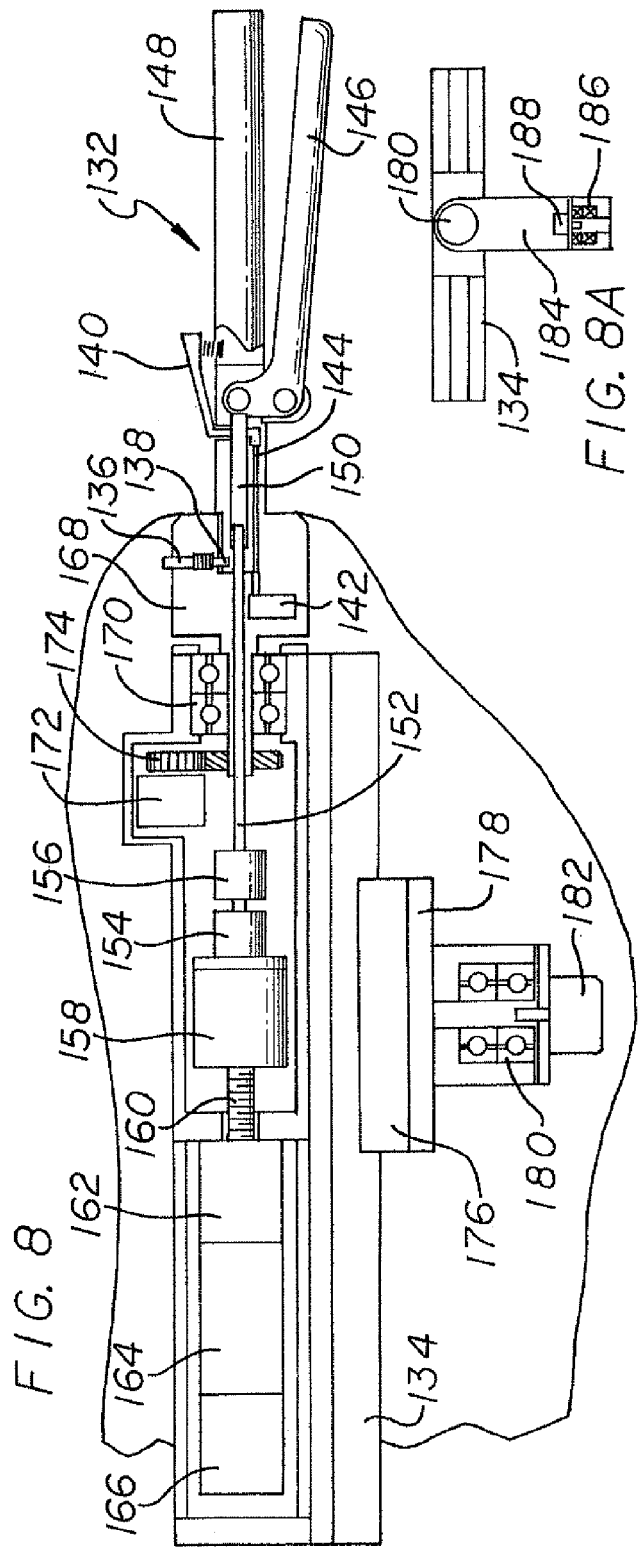
FIG. 7
FIG. 8
FIG. 8A

CORONARY ARTERY

INTERNAL MAMMARY ARTERY

METHOD FOR OPERATING A MEDICAL ROBOTIC SYSTEM BY STOPPING MOVEMENT OF A SURGICAL INSTRUMENT ABOUT A PIVOT POINT OR ISSUING A WARNING IF THE PIVOT POINT MOVES BEYOND A THRESHOLD VALUE

REFERENCE TO CROSS-RELATED APPLICATIONS

This is a continuation of application Ser. No. 11/357,383, filed on Feb. 17, 2006, now U.S. Pat. No. 7,390,325 which is a continuation of application Ser. No. 10/310,405, filed on Dec. 4, 2002, U.S. Pat. No. 7,027,892, which is a continuation of application Ser. No. 09/000,934, filed on Dec. 30, 1997, U.S. Pat. No. 6,905,491, which is a continuation of application Ser. No. 08/603,543, filed on Feb. 20, 1996, U.S. Pat. No. 5,762,458, and a continuation-in-part of application Ser. No. 08/903,914, filed on Jul. 31, 1997, U.S. Pat. No. 5,815,640, which is a continuation of application Ser. No. 08/613,866, filed on Mar. 11, 1996, U.S. Pat. No. 5,907,664, which is a continuation of application Ser. No. 08/072,982, filed on Jun. 3, 1993, U.S. Pat. No. 5,524,180, which is a continuation-in part of application Ser. No. 08/005,604, filed on Jan. 19, 1993, abandoned, which is a continuation-in-part of application Ser. No. 07/927,801, filed on Aug. 10, 1992, abandoned.

BACKGROUND OF THE INVENTION

1. Field of the Invention

The present invention relates to a system and method for performing minimally invasive cardiac procedures.

2. Description of Related Art

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and an endoscope through small incision in the skin of the patient. Manipulating such instruments can be awkward, particularly when suturing a graft to an artery. It has been found that a high level of dexterity is required to accurately control the instruments. Additionally, human hands typically have at least a minimal amount of tremor. The tremor further increases the difficulty of performing minimal invasive cardiac procedures. It would be desirable to provide a system for effectively performing minimally invasive coronary artery bypass graft procedures.

BRIEF SUMMARY OF THE INVENTION

The present invention is a system for performing minimally invasive cardiac procedures. The system includes a pair of surgical instruments that are coupled to a pair of robotic arms. The instruments have end effectors that can be manipulated to hold and suture tissue. The robotic arms are coupled to a pair of master handles by a controller. The handles can be moved by the surgeon to produce a corresponding movement of the end effectors. The movement of the handles is scaled so that the end effectors have a corresponding movement that is different, typically smaller, than the movement performed by the hands of the surgeon. The scale factor is adjustable so that the surgeon can control the resolution of the end effector movement. The movement of the end effector can be controlled by an input button, so that the end effector only moves when the button is depressed by the surgeon. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 7 is an exploded view of an end effector of the system;

FIG. 8 is a top view of a master handle of the system;

FIG. 8a is a side view of the master handle;

DETAILED DESCRIPTION OF THE INVENTION

Figure 1:
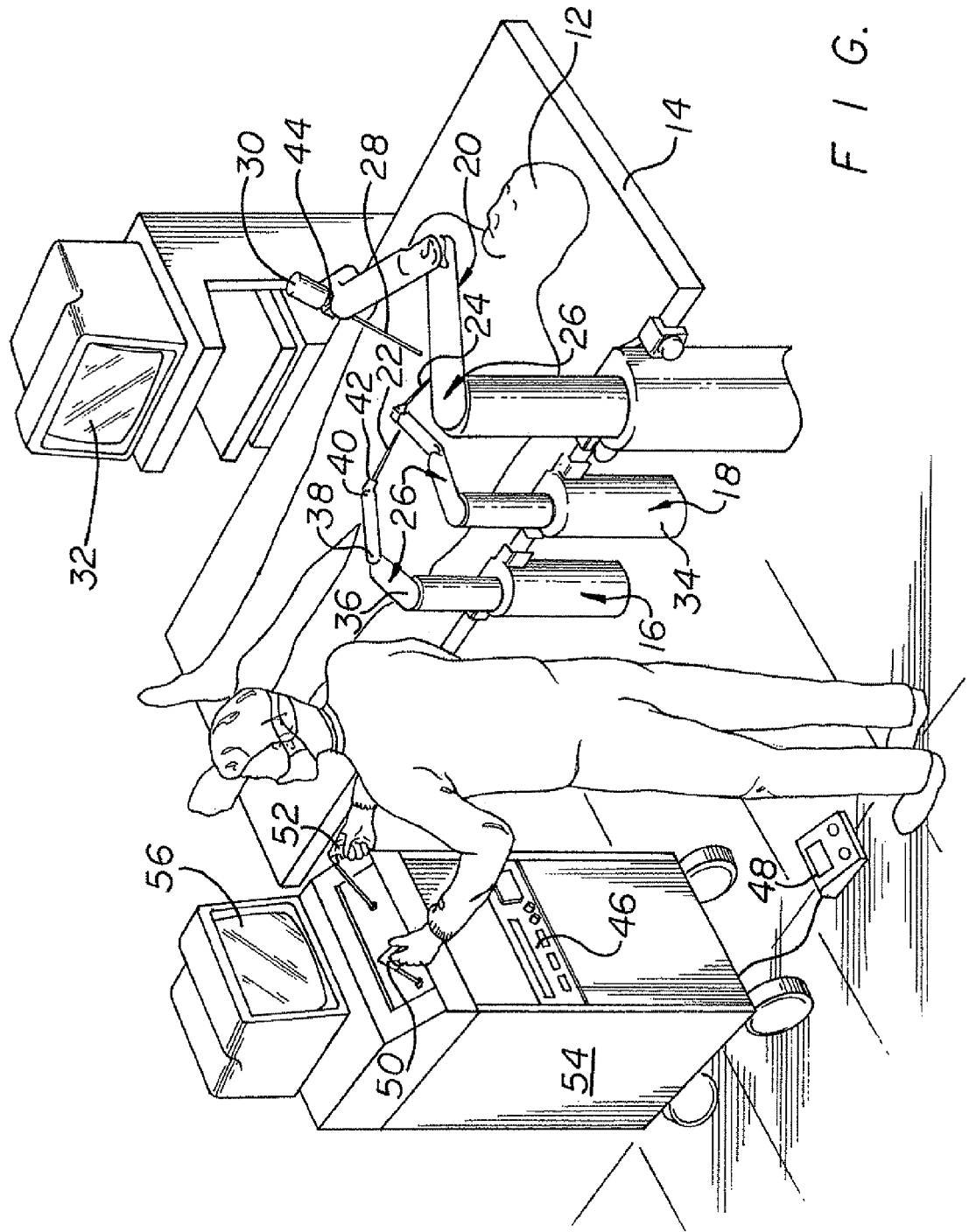
FIG. 1 is a perspective view of a minimally invasive surgical system of the present invention.

Referring to the drawings more particularly by reference numbers, FIG. 1 shows a system 10 that can perform minimally invasive surgery. In the preferred embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels.

The system 10 is used to perform a procedure on a patient 12 that is typically lying on an operating table 14. Mounted to the operating table 14 is a first articulate arm 16, a second articulate arm 18 and a third articulate arm 20. The articulate arms 16-20 are preferably mounted to the table so that the arms are at a same reference plane as the patient. Although three articulate arms are shown and described, it is to be understood that the system may have any number of arms.

The first and second articulate arms 16 and 18 each have a surgical instrument 22 and 24 coupled to a robotic arm 26. The third articulate arm 20 has an endoscope 28 that is held by a robotic arm 26. The instruments 22 and 24, and endoscope 28 are inserted through incisions cut into the skin of the patient. The endoscope has a camera 30 that is coupled to a television monitor 32 which displays images of the internal organs of the patient.

The robotic arms 26 each have a linear motor 34, a first rotary motor 36 and a second rotary motor 38. The robotic arms 26 also have a pair of passive joints 40 and 42. The articulate arm 20 also have a worm gear 44 and means to couple the instruments 22 and 24, and endoscope 28 to the robotic arm 26. The first, second, and third articulate arms are coupled to a controller 46 which can control the movement of the arms.

The controller 46 is connected to an input device 48 such as a foot pedal that can be operated by a surgeon to move the location of the endoscope and view a different portion of the patient by depressing a corresponding button(s) of the foot pedal 48. The controller 46 receives the input signals from the foot pedal 48 and moves the robotic arm 26 and endoscope 28 in accordance with the input commands of the surgeon. The robotic arms may be devices that are sold by the assignee of the present invention, Computer Motion, Inc. of Goleta, Calif., under the trademark AESOP. The system is also described in allowed U.S. application Ser. No. 08/305,415, which is hereby incorporated by reference. Although a foot pedal 46 is shown and described, it is to be understood that the system may have other input means such as a hand controller, or a speech recognition interface.

The instruments 22 of the first 16 and second 18 articulate arms are controlled by a pair of master handles 50 and 52 that can be manipulated by the surgeon. The handles 50 and 52, and arms 16 and 18, have a master-slave relationship so that movement of the handles produces a corresponding movement of the surgical instruments. The handles 50 and 52 may be mounted to a portable cabinet 54. A second television monitor 56 may be placed onto the cabinet 54 and coupled to the endoscope 28 so that the surgeon can readily view the internal organs of the patient. The handles 50 and 52 are also coupled to the controller 46. The controller 46 receives input signals from the handles 50 and 52, computes a corresponding movement of the surgical instruments, and provides output signals to move the robotic arms and instruments.

Figure 2:
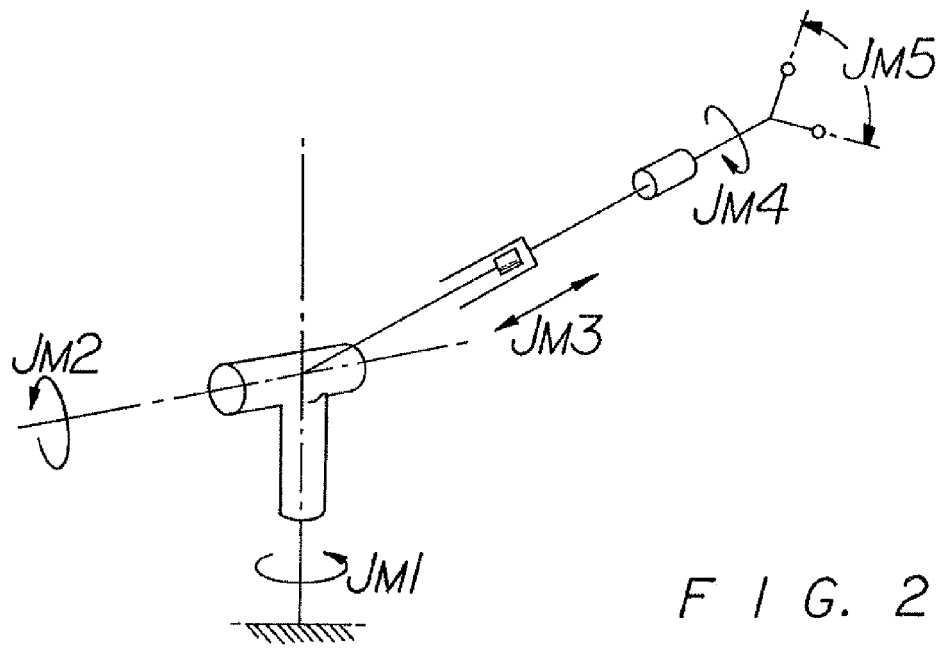
FIG. 2 is a schematic of a master of the system.

Each handle has multiple degrees of freedom provided by the various joints Jm1-Jm5 depicted in FIG. 2. Joints Jm1 and Jm2 allow the handle to rotate about a pivot point of the cabinet 54. Joint Jm3 allows the surgeon to move the handle into and out of the cabinet 54 in a linear manner. Joint Jm4 allows the surgeon to rotate the master handle about a longitudinal axis of the handle. The joint Jm5 allows a surgeon to open and close a gripper. Each joint Jm1-Jm5 has a position sensor which provides feedback signals that correspond to the relative position of the handle. The position sensors may be potentiometers, or any other feedback device, that provides an electrical signal which corresponds to a change of position.

Figure 3:
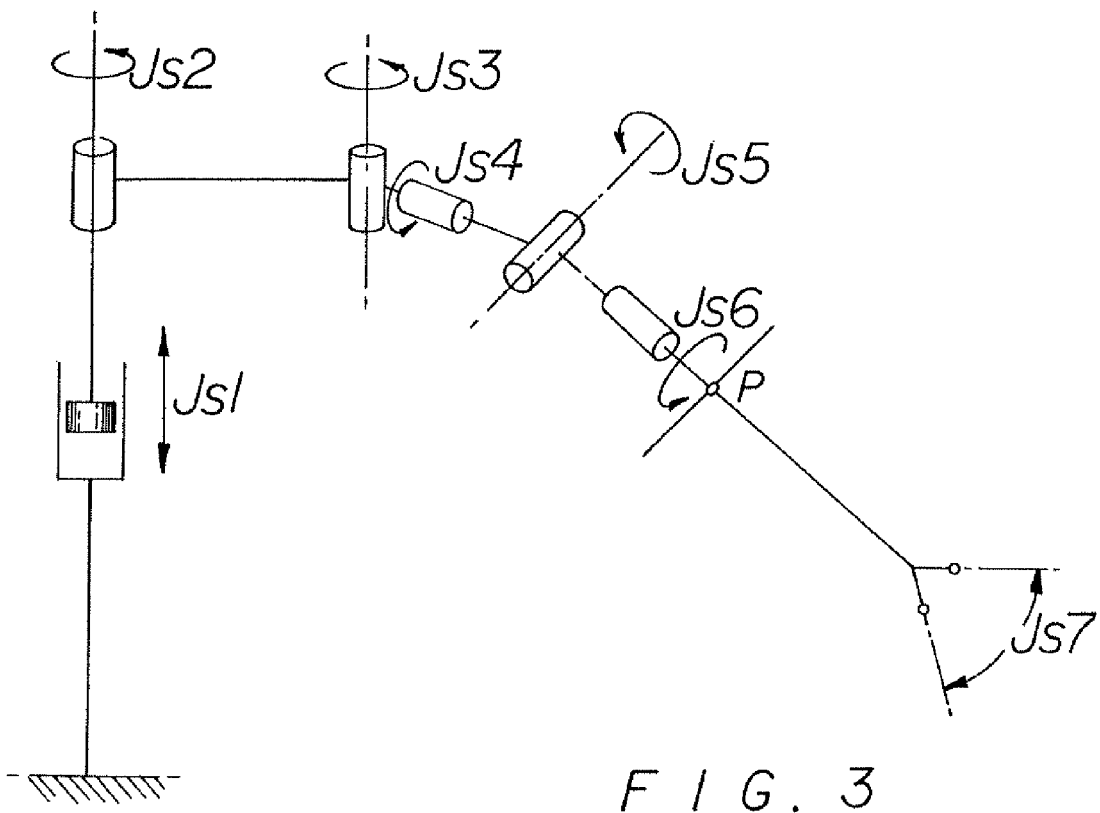
FIG. 3 is a schematic of a slave of the system.

FIG. 3 shows the various degrees of freedom of each articulate arm 16 and 18. The joints Js1, Js2 and Js3 correspond to the linear motor and rotary motors of the robotic arms 26, respectively. The joints Js4 and Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Figure 4:
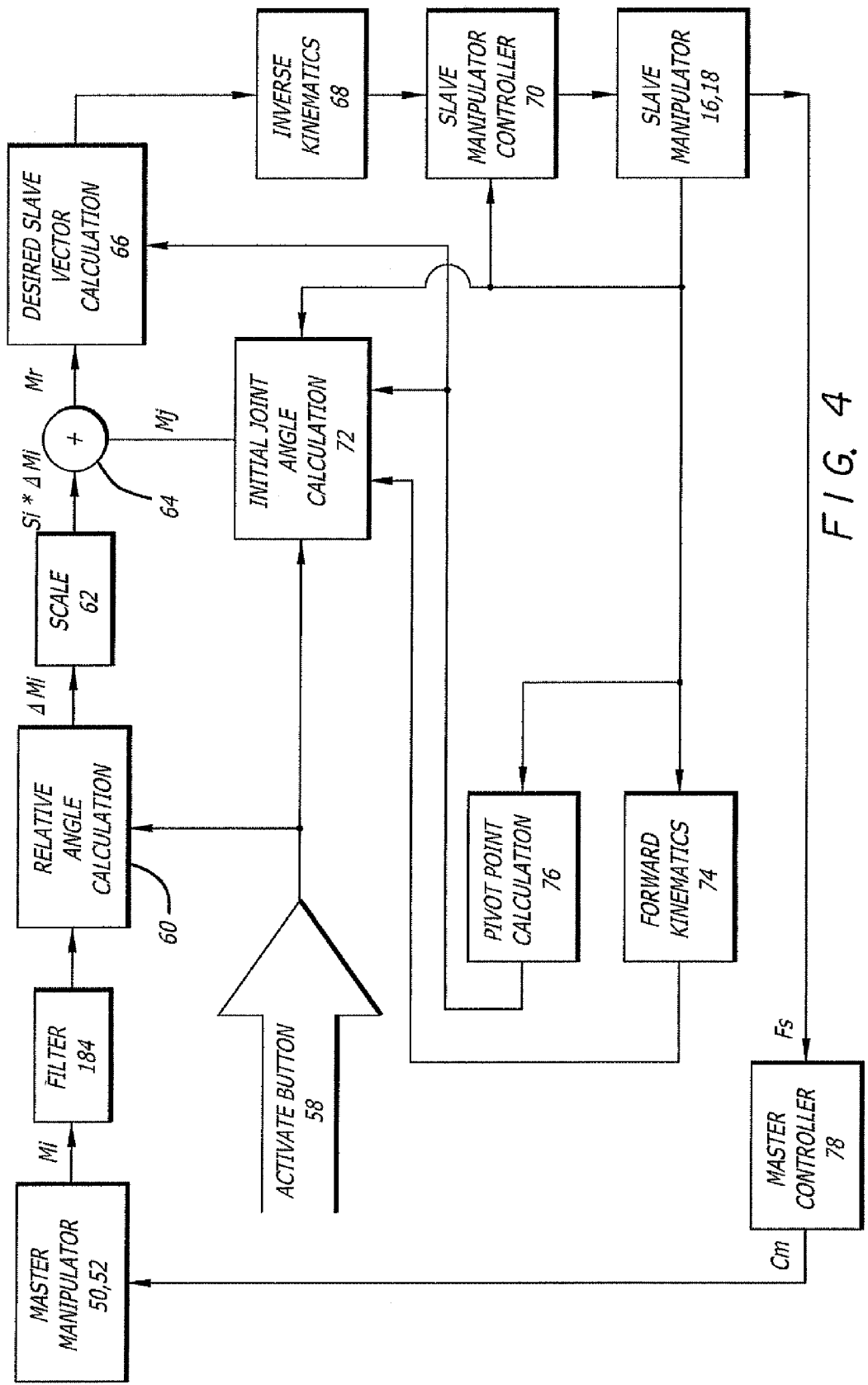
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button is shown and described, it is to be understood that the surgical instrument may be activated by other means such as voice recognition. The input button may be latched so that activation of the instrument toggles between active and inactive each time the button is depressed by the surgeon.

When the surgeon moves a handle, the position sensors provide feedback signals M1-M5 that correspond to the movement of the joints Jm1-Jm5, respectively. The controller 46 computes the difference between the new handle position and the original handle position in computation block 60 to generate incremental position values $\Delta M1$-$\Delta M5$.

The incremental position values $\Delta M1$-$\Delta M5$ are multiplied by scale factors S1-S5, respectively in block 62. The scale factors are typically set at less than one so that the movement of the instrument is less than the movement of the handle. In this manner the surgeon can produce very fine movements of the instruments with relatively coarse movements of the handles. The scale factors S1-S5 are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one described, it is to be understood that a scale factor may be greater than one. For example, it may be desirable to spin the instrument at a greater rate than a corresponding spin of the handle.

The controller 46 adds the incremental values $\Delta M1$-$\Delta M5$ to the initial joint angles Mj1-Mj5 in adder element 64 to provide values Mr1-Mr5. The controller 46 then computes desired slave vector calculations in computation block 66 in accordance with the following equations.

$$Rdx = Mr3 \cdot \sin(Mr1) \cdot \cos(Mr2) + Px$$

$$Rdy = Mr3 \cdot \sin(Mr1) \cdot \sin(Mr2) + Py$$

$$Rdz = Mr3 \cdot \cos(Mr1) + Pz$$

$$Sdr = Mr4$$

$$Sdg = Mr5$$

where;

Rdx, y, z=the new desired position of the end effector of the instrument.

Sdr=the angular rotation of the instrument about the instrument longitudinal axis.

Sdg=the amount of movement of the instrument fingers.

Px, y, z=the position of the pivot point P.

The controller 46 then computes the movement of the robotic arm 26 in computational block 68 in accordance with the following equations.

$$Jsd1 = Rdz$$

$$Jsd3 = p - \cos^{-1}\left[\frac{Rdx^2 + Rdy^2 - L1^2 - L2^2}{2L1 \times L2}\right]$$

$$Jsd2 = \tan^{-1}(Rdy/Rdx) + D \text{ for } Jsd3 \leq 0$$
$$Jsd2 = \tan^{-1}(Rdy/Rdx) - D \text{ for } Jsd3 > 0$$

$$D = \cos^{-1}\left[\frac{Rdx^2 + Rdy^2 - L1^2 - L2^2}{2 \times L1\sqrt{Rdx^2 + Rdy^2}}\right]$$

$$Jsd6 = Mr4$$
$$Jsd7 = Mr5$$

where;
Jsd1=the movement of the linear motor.
Jsd2=the movement of the first rotary motor.
Jsd3=the movement of the second rotary motor.
Jsd6=the movement of the rotational motor.
Jsd7=the movement of the gripper.
L1=the length of the linkage arm between the first rotary motor and the second rotary motor.
L2=the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases the input button and moves the handle. When the input button 58 is initially depressed, the controller 46 computes initial joint angles Mj1-Mj5 in computational block 72 with the following equations.

$$Mj1 = \tan^{-1}(ty/tx)$$
$$Mj2 = \tan^{-1}(d/tz)$$
$$Mj3 = D$$
$$Mj4 = Js6$$
$$Mj5 = Js7$$
$$d = \sqrt{tx^2 + ty^2}$$
$$tx = \frac{Rsx - Px}{D} \quad ty = \frac{Rsy - Py}{D} \quad tz = \frac{Rsz - Pz}{D}$$
$$D = \sqrt{(Rsx - Px)^2 + (Rsy - Py)^2 + (Rsz - Pz)^2}$$

The forward kinematic values are computed in block 74 with the following equations.

$$Rsx = L1 \cdot \cos(Js2) + L2 \cdot \cos(Js2 + Js3)$$
$$Rsy = L1 \cdot \cos(Js2) - L2 \cdot \sin(Js2 + Js3)$$
$$Rsz = J1$$

Figure 5:
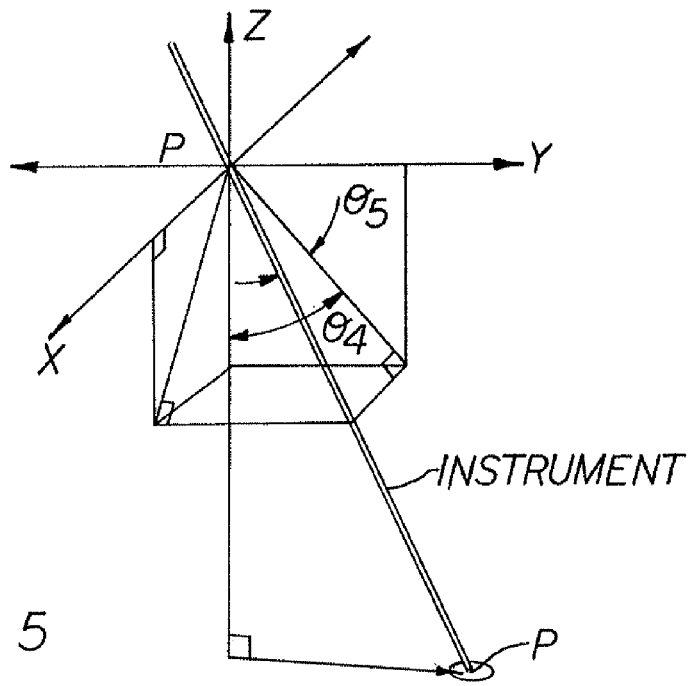
FIG. 5 is a schematic showing the instrument in a coordinate frame.

The joint angles Mj are provided to adder 64. The pivot points Px, Py and Pz are computed in computational block 76 as follows. The pivot point is calculated by initially determining the original position of the intersection of the end effector and the instrument PO, and the unit vector Uo which has the same orientation as the instrument. The position P(x, y, z) values can be derived from various position sensors of the robotic arm. Referring to FIG. 5 the instrument is within a first coordinate frame (x, y, z) which has the angles θ4 and θ5. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument $\Delta\theta$ is computed by taking the arcsin of the cross-product of the first and second unit vectors Uo and U1 of the instrument in accordance with the following line equations Lo and L1.

$$\Delta\theta = \arcsin(|T|)$$

$$T = Uo \times U1$$

where;
T=a vector which is a cross-product of unit vectors Uo and U1.

Figure 6:
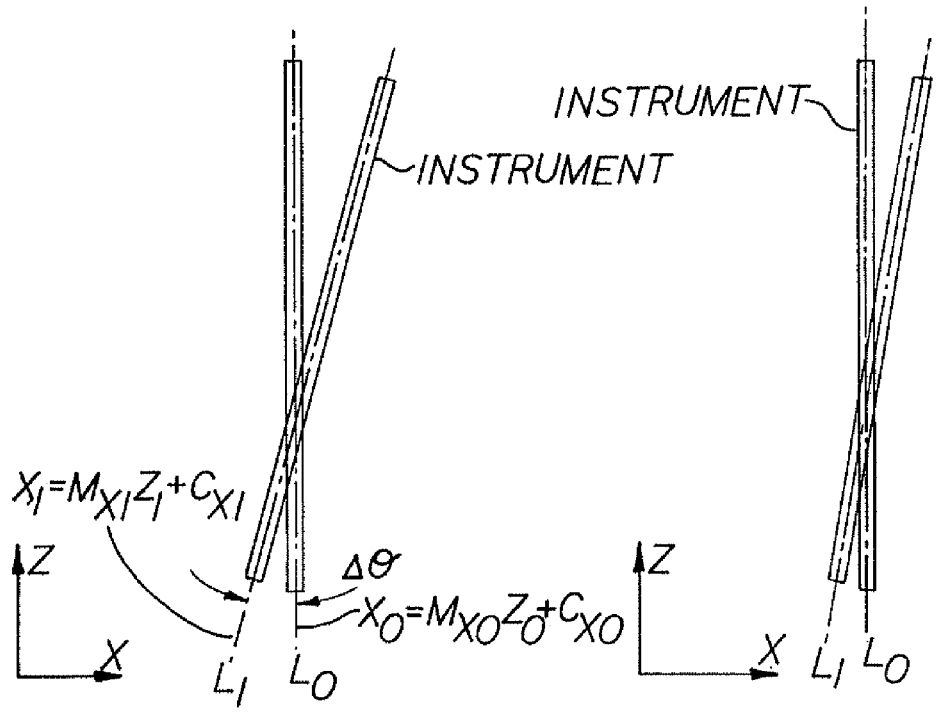
FIG. 6 is a schematic of the instrument moving about a pivot point.
Figure 9:
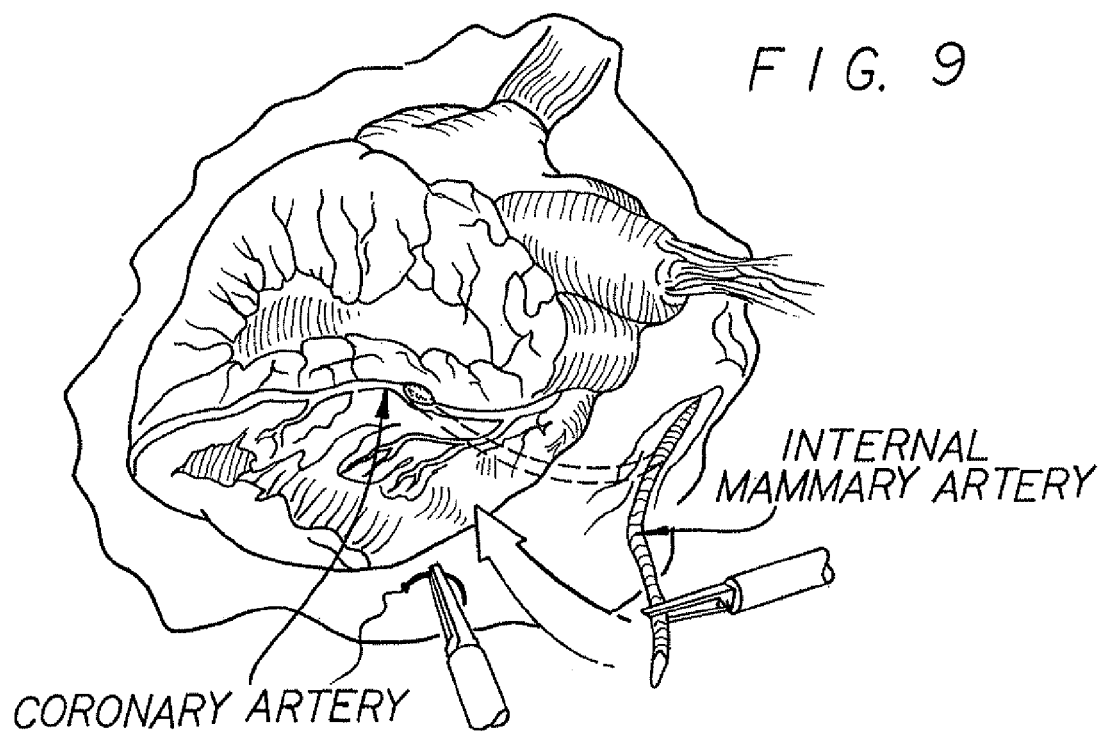
FIGS. 9-10A-I are illustrations showing an internal mammary artery being grafted to a coronary artery.

The unit vector of the new instrument position U1 is again determined using the positions sensors and the transformation matrix described above. If the angle $\Delta\theta$ is greater than a threshold value, then a new pivot point is calculated and Uo is set to U1. As shown in FIG. 6, the first and second instrument orientations can be defined by the line equations Lo and L1:

$$xo = Mxo \cdot Zo + Cxo$$
$$yo = Myo \cdot Zo + Cyo \qquad \qquad \text{Lo}$$
$$x1 = Mx1 \cdot Z1 + Cx1$$
$$y1 = My1 \cdot Z1 + Cy1 \qquad \qquad \text{L1}$$

where;
Zo=a Z coordinate along the line Lo relative to the z axis of the first coordinate system.
Z1=a Z coordinate along the line L1 relative to the z axis of the first coordinate system.
Mxo=a slope of the line Lo as a function of Zo.
Myo=a slope of the line Lo as a function of Zo.
Mx1=a slope of the line L1 as a function of Z1.
My1=a slope of the line L1 as a function of Z1.
Cxo=a constant which represents the intersection of the line Lo and the x axis of the first coordinate system.
Cyo=a constant which represents the intersection of the line Lo and the y axis of the first coordinate system.
Cx1=a constant which represents the intersection of the L1 and the x axis of the first coordinate system.
Cy1=a constant which represents the intersection of the line L1 and the y axis of the first coordinate system.

The slopes are computed using the following algorithms:

$$Mxo = Uxo/Uzo$$

$$Myo = Uyo/Uzo$$

$$Mx1 = Ux1/Uzi$$

$$My1 = Uy1/Uz1$$

$$Cx0 = Pox - Mx1 \cdot Poz$$

$$Cy0 = Poy - My1 \cdot Poz$$

$$Cx1 = P1x - Mx1 \cdot P1z$$

$$Cy1 = P1y - My1 \cdot P1z$$

where;
- Uo (x, y and z)=the unit vectors of the instrument in the first position within the first coordinate system.
- U1 (x, y and z)=the unit vectors of the instrument in the second position within the first coordinate system.
- Po (x, y and z)=the coordinates of the intersection of the end effector and the instrument in the first position within the first coordinate system.
- P1 (x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance halfway between the two points Ro and R1 is computed and stored as the pivot point $R_{ave}$ of the instrument. The pivot point $R_{ave}$ is determined by using the cross-product vector T.

To find the points Ro and R1 the following equalities are set to define a line with the same orientation as the vector T that passes through both Lo and L1.

$$tx = Tx/Tz$$

$$ty = Ty/Tz$$

where;
- tx=the slope of a line defined by vector T relative to the Z-x plane of the first coordinate system.
- ty=the slope of a line defined by vector T relative to the Z-y plane of the first coordinate system.
- Tx=the x component of the vector T.
- Ty=the y component of the vector T.
- Tz=the z component of the vector T.

Picking two points to determine the slopes Tx, Ty and Tz (e.g. Tx=x1−xo, Ty=y1−yo and Tz=z1−z0) and substituting the line equations Lo and L1, provides a solution for the point coordinates for Ro (xo, yo, zo) and R1 (x1, y1, z1) as follows.

$$zo = ((Mx1-tx)z1 + Cx1 - Cxo)/(Mxo-tx)$$

$$z1 = ((Cy1-Cyo)(Mxo-tx) - (Cx1-Cxo)(Myo-ty))/((Myo-ty)(Mx1-tx) - (My1-ty)(Mxo-tx))$$

$$yo = Myo \cdot zo + Cyo$$

$$y1 = My1 \cdot z1 + Cy1$$

$$xo = Mxo \cdot zo + Cxo$$

$$x1 = Mx1 \cdot z1 + Cx1$$

The average distance between the pivot points Ro and R1 is computed with the following equation and stored as the pivot point of the instrument.

$$R_{ave} = ((x1+xo)/2, (y1+yo)/2, (z1+zo)/2)$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

FIG. 7 shows a preferred embodiment of an end effector 80. The end effector 80 includes a tool 82 that is coupled to an arm 84 by a sterile coupler 86. The tool 82 has a first finger 88 that is pivotally connected to a second finger 90. The fingers can be manipulated to hold objects such as tissue or a suturing needle. The inner surface of the fingers may have a texture to increase the friction and grasping ability of the tool. The first finger 88 is coupled to a rod 92 that extends through a center channel 94 of the tool 82. The tool 82 may have an outer sleeve 96 which cooperates with a spring biased ball quick disconnect fastener 98 of the sterile coupler 86. The quick disconnect allows tools other than the finger grasper to be coupled to an arm. For example, the tool 82 may be decoupled from the coupler and replaced by a cutting tool. The coupler 86 allows the surgical instruments to be interchanged without having to re-sterilize the arm each time an instrument is plugged into the arm.

The sterile coupler 86 has a slot 100 that receives a pin 102 of the arm 84. The pin 102 locks the coupler 86 to the arm 84. The pin 102 can be released by depressing a spring biased lever 104. The sterile coupler 86 has a piston 106 that is attached to the tool rod and in abutment with an output piston 108 of a load cell 110 located within the arm 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire arm 82 is rotated by a motor drive worm gear 122. In operation, the motor receives input commands from the controller 46 and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46. The arm 84 may be covered with a sterile drape 124 so that the arm does not have to be sterilized after each surgical procedure.

FIGS. 8 and 8a show a preferred embodiment of a master handle assembly 130. The assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled to a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. The swivel movement is translated to a corresponding spin of the end effector by the controller and robotic arm.

The arm 134 may be coupled to a linear bearing 176 and corresponding position sensor 178 which allow and sense linear movement of the handle. The linear movement of the handle is translated into a corresponding linear movement of the end effector by the controller and robotic arm. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm.

A human hand will have a natural tremor typically resonating between 6-12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6-12 hertz.

As shown in FIGS. 9 and 10A-I the system is preferably used to perform a cardiac procedure such as a coronary artery bypass graft (CABG). The procedure is performed by initially cutting three incisions in the patient and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery.

Figure 10A:
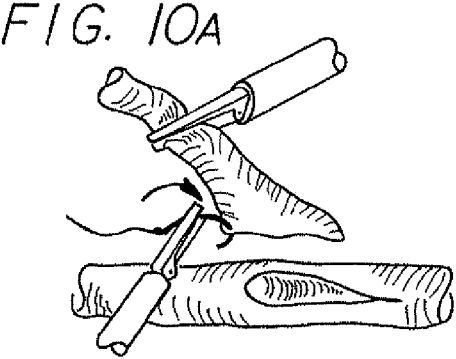
Figure 10B:
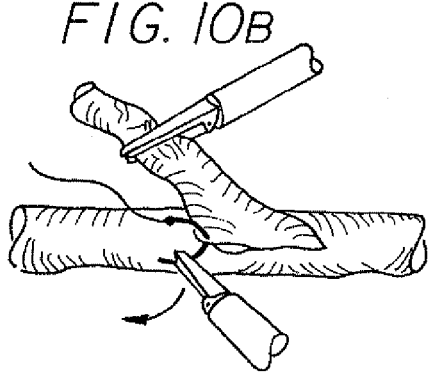
Figure 10C:
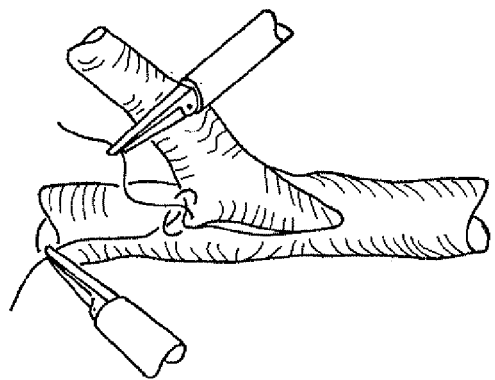
Figure 10D:
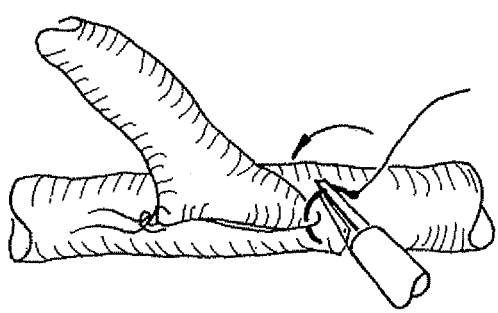
Figure 10E:
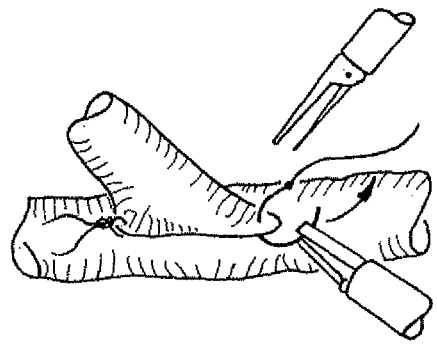
Figure 10F:
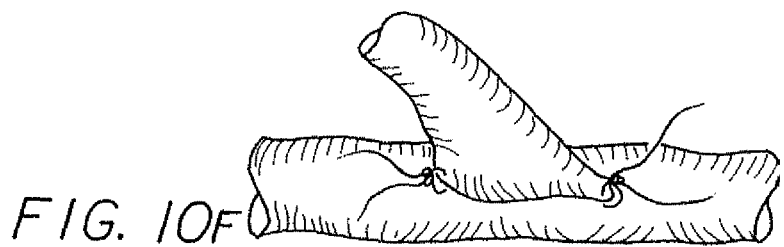
Figure 10G:
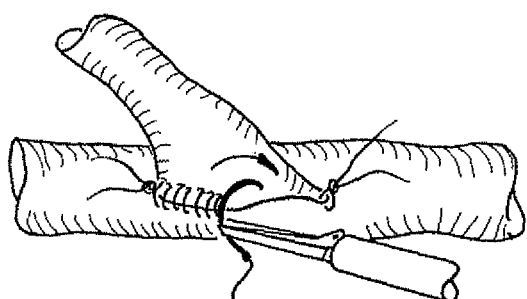
Figure 10H:
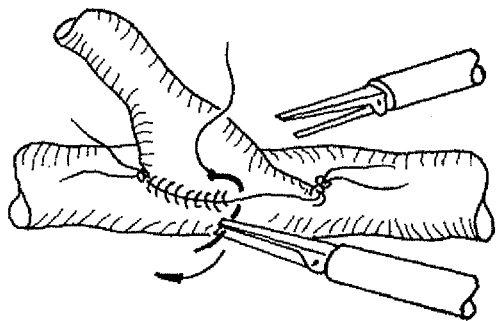
Figure 10I:
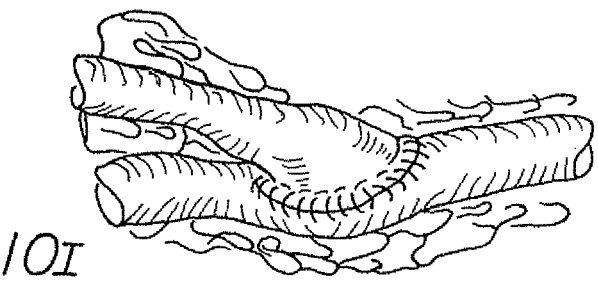

Referring to FIGS. 10A-I, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D-F, a new needle and thread can be inserted into the chest cavity to suture the toe of the graft artery to the coronary artery. As shown in FIG. 10H-I, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method implemented in a controller for operating a medical robotic system, comprising:
   receiving information from a first set of sensors indicating sensed movement of an input device;
   commanding a robotic arm to move a surgical instrument about a pivot point in response to the received information indicating sensed movement of the input device;
   receiving information from a second set of sensors indicating sensed movement of the robotic arm;
   determining whether the pivot point moves more than a threshold value using the received information indicating sensed movement of the robotic arm; and
   commanding the robotic arm to stop movement of the surgical instrument about the pivot point if the pivot point moves more than the threshold value.

2. A method implemented in a controller for operating a medical robotic system, comprising:
   receiving information from a first set of sensors indicating sensed movement of an input device;
   commanding a robotic arm to move a surgical instrument about a pivot point in response to the received information indicating sensed movement of the input device;
   receiving information from a second set of sensors indicating sensed movement of the robotic arm;
   determining whether the pivot point moves more than a threshold value using the received information indicating sensed movement of the robotic arm; and
   issuing a warning if the pivot point moves more than the threshold value.

* * * * *